Figure 1:
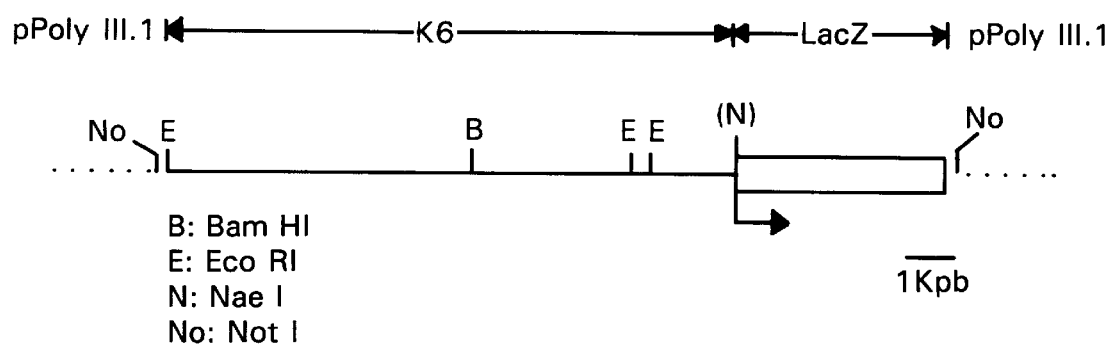

United States Patent
Merino et al.

[11] Patent Number: 6,087,554
[45] Date of Patent: *Jul. 11, 2000

[54] TRANSGENIC ANIMALS FOR THE DETERMINATION OF AGENTS WHICH STIMULATE OR REPRESS EPIDERMAL HYPERPROLIFERATION AND HAIR GROWTH

[75] Inventors: Angel Ramirez Merino; Miguel Angel Vidal Caballero, both of Madrid; Ana M$^a$ Bravo Moral, Leon; José Luis Jorcano Noval, Las Rozas, all of Spain

[73] Assignee: Centro de Investigaciones Energeticas, Medioambeintales Y Tecnologicas (C.I.E.M.A.T.), Madrid, Spain

[ * ] Notice: This patent issued on a continued prosecution application filed under 37 CFR 1.53(d), and is subject to the twenty year patent term provisions of 35 U.S.C. 154(a)(2).

[21] Appl. No.: 08/861,920

[22] Filed: May 22, 1997

Related U.S. Application Data

[63] Continuation of application No. 08/424,239, Apr. 19, 1995, abandoned, which is a continuation of application No. 08/157,390, Nov. 23, 1993, abandoned.

[30] Foreign Application Priority Data

Mar. 29, 1993 [ES] Spain ..................... 9300643

[51] Int. Cl.$^7$ .............................. C12N 5/00; C12N 15/00
[52] U.S. Cl. .................................. 800/18; 800/3
[58] Field of Search ................ 800/2, DIG. 1, 800/18, 3; 435/172.3, 320.1; 536/24.1; 424/9.2; 935/34, 59

[56] References Cited

PUBLICATIONS

A Fire et al (1990) Gene 93: 189–198.
RM Strojek et al (1988) Genetic Engineering:Principles and Methods. v. 10 pp. 221–246 Plenum Press.
M Blessing et al (1987) EMBO J 6:567–575.
C–K Jiang et al (1991) J. Investigative Dermatology 96:162–167.
M Blessing et al (1989) EMBO J. 8: 117–126.
M Abe et al (1990) J Cell Biol 111: 1197–1206.

*Primary Examiner*—Bruce R. Campell
*Attorney, Agent, or Firm*—Fish & Richardson, P.C.

[57] ABSTRACT

A vertebrate, non-human transgenic animal whose cells, both somatic and germinal, contain a recombinant genetic construction formed of a marker gene and a regulator region capable of being induced in the epidermis of said transgenic animal in response to hyperproliferative stimuli, the genetic construction of which has been introduced into the animal or into an antecessor of the animal in an embryonic stage. The genetic construction is induced also in the bulb of the hair in the phase of active growth or anagen. The said genetic construction consists of a marker gene characterized by the fact that it is easily detectable, under the control of the regulator region of the gene of the K6 keratin, this protein being characterized by its ability to be induced in the suprabasal layers of the epidermis in response to hyperproliferative stimuli both endogenous (tumors, cicatrization of wounds, diseases which, such as psoriasis, produce hyperproliferation, etc.) and exogenous (topical treatments with retinoic acid, TPA, etc.). Therefore, transgenic animals carrying this genetic construction in their genome are useful in the identification of physical, chemical or biological agents which lead to epidermal hyperproliferation and growth of the hair, or inhibit these processes.

6 Claims, 1 Drawing Sheet

TRANSGENIC ANIMALS FOR THE DETERMINATION OF AGENTS WHICH STIMULATE OR REPRESS EPIDERMAL HYPERPROLIFERATION AND HAIR GROWTH

This is a continuation of application Ser. No. 08/424,239, filed Apr. 19, 1995, now abandoned, which is a continuation of application Ser. No. 08/157,390, filed Nov. 23, 1993, now abandoned.

The present invention refers to nonhuman transgenic animals which can be used as model system for the identification of agents which induce or repress epidermal hyperproliferation, such as, for instance, radiations, chemical and cosmetic compounds, pathologies, etc. The invention is also useful for the detection of agents which influence the hair cycle.

Transgenic animals are animals which bear an exogenous gene (called transgene) in their genome which has been introduced either in them themselves or in an predecessor. Due to the fact that the exogenous gene is also present in the germ cells of these animals, the transgene is transmitted from parent to children so that it is possible to establish lines of transgenic animals from a first founder animal. The introduction of the transgene into the fertilized oocyte maximizes the possibilities of the transgene being present in all the cells, both somatic and germinal, of the founder animal. The latter will transmit the transgene to approximately half of its descendants, which will carry it in all its cells. If the transgene is introduced in a later embryonic stage, the founder animal would be a mosaic since not all its somatic and germinal cells will carry the transgene. This would have the result that a smaller proportion of descendants carries the transgene; however, the descendants which inherit it would carry in all their cells, including the germ cells.

One problem when transgenic animals are generated is that not all of them are founders and therefore the corresponding lines generated from them express the transgene which they carry. This effect, known as position effect, is due to the fact that the transgene can be integrated in any place of the genome of the transgenic animal. If the integration takes place in a heterochromatin region, the activity of the transgene may be suppressed in whole or in part. Alternatively, if the transgene is integrated near the regulator region of a gene, the activity of the transgene may be altered or even come to be controlled by this "foreign" regulator region instead of by the one which it bears. For this reason, once the transgenic animals have been identified, it is necessary to proceed to determine in which of them the transgene is suitably expressed.

Although it is possible to generate transgenic animals of different species, most of the work in this field has been done with mice. Transgenic animals in general, and mice in particular, are of great utility as model systems for studying the mechanisms which regulate the control of the genetic activity, as well as for determining the role of specific factors in animal physiology and their alterations.

Although there are various possibilities, the most usual manner of introducing the transgene is by microinjection of DNA in the pronucleus of embryos in the single-cell state (Gordon et al., 1980, Proc. Natl. Acad. Sci., U.S.A. 77:7380; Brinster et al., 1981, Cell 27:223; Wagner et al., 1981, Proc. Natl. Acad. Sci. U.S.A. 78:6376;

Gordon and Ruddle, 1981, Methods Enzymol. 101C:411). Up to the present time, a considerable number of genes have bean introduced and studied in transgenic animals, basically mice (for a survey, see Palmiter and Gordon, 1986, Ann. Rev. Genet. 20:405). There have also been introduced into transgenic animals recombinant genetic constructions which contain a regulator region and a coding region for a protein which come from different sources. These "compound" transgenes, although present in all the cells of the animal, are only expressed in those tissues which normally activate the specific regulator element used in the genetic construction. In this way, using suitable regulator elements, it is possible to direct the activity of genes of varied interest (clinical, pharmaceutical, biological or biotechnological) to preselected tissues of the transgenic animal. One class of particularly interesting regulator sequences is those which are inducible, due to the fact that they make it possible to regulate the expression of the structural gene to which they are attached, controlling the presence or absence of the inductor required in order to activate said regulator regions.

The generation of transgenic animals is well-established and is known to the corresponding experts (Gorton and Ruddle, 1983, Methods in Enzymol. 101C:1244; Hogan, Constatini and Lacy, 1986, *Manipulating a Mouse Embryo. A Laboratory Manual*. Cold Spring Harbor Laboratory, Cold Spring Harbor).

Skin is the tissue which covers the surface of the body, it being formed of two main layers—the surface epithelium or epidermis and the underlying conjunctive tissue layer or dermis (Fawcett, 1986, in "Bloom and Fawcett, A Textbook of Histology," 11th Edition, published by W. B. Saunders Company, pages 543–575).

The specific functions of the skin depend to a great extent on the properties of the epidermis. This epithelium forms a continuous cellular cover over the entire surface of the body but is specialized also to form certain cutaneous appendages—the hair, the nails and the glands.

The epidermis is a stratified flat epithelium which is divided into two cell layers: the basal layer, formed of a single layer of cuboid cells which have the ability to divide, and the suprabasal layer, formed of cells coming from the basal layer and which have lost the ability to divide. In the suprabasal layer, one can distinguish prickle-cell, granular and horny layers. The suprabasal cells are embarked in a program of terminal differentiation during which, instead of migrating towards the surface of the epithelium, suffer drastic morphological changes which finally give rise to the corneocytes of the horny layer. These flat, strongly keratinized dead cells finally become detached from the skin by desquamation.

Hairs are thin filaments of keratin which arise from a tubular invagination of the epidermis, the hair follicle, which extends deep down to the dermis. The hairs are developed from the invagination of the bulbous terminal expansion of the active follicle. Both the hair proper and the follicle which surrounds it are complex structures formed by several different concentric cellular layers (Fawcett, 1987, op. cit.).

The hair is not an organ which grows continuously, but rather alternates phases of growth with periods of rest, greatly varying the structure of the follicle in accordance with the stage of growth of the hair. Thus, in the growth phase, the follicle is lengthened until reaching its maximum length while the epithelial cells which surround the dermal papilla are differentiated in their various characteristic types. The cells of the matrix, in the invagination which surrounds the dermal papilla, start to proliferate actively. The cells derived from the matrix also maintain a high mitotic index while keratinized in the keratogenic zone of the bulb, immediately above the dome of the dermal papilla, giving rise to the hair stem with its three main components: medulla, cortex and cuticle.

Most, if not all, cells of vertebrates contain a cytoskeleton formed by the so-called intermediate filaments. This cytoskeleton can be formed by at least six different classes of proteins which are expressed in a specific manner for each cellular type. The keratins form the cytoskeleton of intermediate filaments of the epithelial cells and their appendages (nails and hairs) (Mol et al., 1982, Cell 31:11; Heid et al., 1986, Differentiation 32:101). These proteins constitute a family of about 30 members which is characterized also because its expression in groups of 2 to 8 polypeptides is specific to each type of epithelial cell. Thus, in the epidermis, the basal cells synthesize the K4 and K14 keratins while, when the cells differentiate to suprabasal, they replace these keratins by the K1 and K10 pair (Eichner et al., 1984, J. Cell Biol. 98:1388 Stoller et al., 1988, J. Cell Biol. 107:427). On the other hand, the K6 keratin which is present in various internal stratified epithelia such as tongue, palate, vagina or the external root layer of the hair follicle, is not expressed in interfollicular epidermis (Quinlan et al., 1985, Annals New York Acad. Sci. 455:282). However, this keratin is induced in the suprabasal cells of the epidermis in all hyperproliferative disorders of this tissue (Weiss et al., 1984, J. Cell. Biol. 98:1397; Stoller et al., op. cit.). This keratin is also induced by topical treatments of the skin with TPA, retinoic acid, and other hyperplasia-inducing agents (see, for example, Schweizer et al., 1987, J. Invest. Dermatol., 125; Eichner et al., 1992, J. Invest. Dermatol., 154).

By everything which has just been described, the DNA sequences which regulate the expression of the gene of the K6 keratin can be identified and they are coupled functionally to form a marker gene in a genetic construction in such a way that the expression of the marker gene remains under the control of the regulator region of the K6 gene, a transgenic animal bearing such construction would be an excellent model system for identifying substances, factors or processes which lead to epidermal hyperproliferation. In the presence of these stimuli, the regulator region of the K6 gene would be activated in the suprabasal layers of the epidermis, which would lead to the synthesis of the product coded by the marker gene, which would easily be detected by methods which are described further below. And the present invention consists precisely in the generation of transgenic animals bearing the transgene formed of the regulator region of the gene of K6 keratin coupled to a suitable marker gene in order to be used to identify physical, chemical, biological agents, etc., which induce epidermal hyperproliferation. Alternatively, these animals also would permit identifying substances and factors which protect the epidermis from the action of hyperproliferative stimuli or which inhibit epidermal hyperproliferation. An animal treated with such an epidermal hyperproliferation protective substances will respond to the hyperproliferative stimuli with less or no intensity than an untreated animal. Accordingly, the K6 regulator region will be induced with less or no intensity, which will be visualized as less or no induction of the corresponding marker gene coupled to it.

For the visualizing of the hyperproliferative state of the epidermis, suitable selection of the marker gene which is to be coupled to the regulator region of the K6 gene is of great importance; said marker must code for an easily identifiable product. In the invention, the gene of β-galactosidase (β-gal) has been selected as marker in order to be placed under the control of the regulator region of the K6 keratin and introduced into the genome of transgenic animals. When the skin of the resultant transgenic animals is subjected to hyperproliferative stimuli in the presence of X-gal, the substrate of β-gal, the epidermal suprabasal cells, including those of the tail, develop a blue color the intensity of which will depend on the intensity of the induction of the transgene, which, in its turn, will depend on the intensity of the hyperproliferative stimulus to which the epidermis has been subjected. In similar manner, there will also be dyed blue all those cells and tissues in which the regulator regions of the gene of the K6 keratin used in the genetic construction is activated, in either a constituent manner or dependent on an inductor stimulus.

Another marker gene of great interest would be that of luciferase (Ow et al., 1986, Science 234:856). Using this marker gene, the cells of the epidermis which is subjected hyperproliferative stimuli will produce luciferase which, in the presence of luciferin and under suitable conditions will result in the emission of light. Other possible marker genes, although probably less interesting in view of the characteristics of this invention would give rise to chemical products biochemically detectable as such, for instance chloramphenicol acetyltransferase (Gorman et al., 1982, Mol. Cell Biol. 2: 1044), xanthine-guanine phosphoribosyl transferase (Nulligan and Berg, 1980, Science 209:1422), the T antigen of virus SV40 or the growth hormone. Other possible marker genes characterized by giving rise to biologically active products such as, for example, oncogenes or cytokines, although possible, would be less useful in the present invention.

Other advantages and characteristics of the invention will become clear from the description of the invention which follows as well as from the claims.

DESCRIPTION OF THE INVENTION

Drawings

FIG. 1 shows the insert of the plasmid pkIV*Z(8.8), consisting of 8.8 kilobase pairs (kpb) of the 5' region which precedes the genes of the bovine keratin IV* to which the coding region of the marker gene of β-galactosidase has been united. Bovine keratin KIV*, so-called for historic reasons, is equivalent to the human K6 (Jorcano et al., Differentiation . . . ). Therefore, throughout this invention, we will speak of the K6 keratin, whether of bovine or human origin. An *E. coli* strain containing plasmid pkIV*Z (8.8) was deposited with National Collections of Industrial and Marine Bacteria Ltd., 23 St. Machar Drive Aberdeen, Scotland as deposit no. NCIMB 40539 on Feb. 25, 1993.

Construction of the Transgene KIV*Z(8.8)

In order to create an inducible gene in the epidermis in response to hyperproliferative stimuli, a DNA fragment of 8.8 Kpb of the 5' region which precedes the gene of the bovine keratin K6 is united to the coding region of the gene of the β-galactosidase in accordance with the recombinant DNA techniques described in Maniatis et al. (1982) *Molecular Cloning: A Laboratory Manual* (Cold Spring Harbor Laboratory, Cold Spring Harbor).

FIG. 1 describes the transgene; in it there are shown the cutting sites of various restriction enzymes as well as the parts which come from the regulator region of the gene of the K6 keratin (K6; continuous line), of the gene of β-galactosidase (lacZ; rectangular zone) and of the vector (pPolyIII.1; broken line).

This construction was carried out in various steps:

Step 1: Cloning of lacZ in the plasmid pPolyIII.1.

Start from the plasmid pRSV-lacZ-pUC8 which contains the lacZ gene bound to the LTR of the RSV virus which are cloned in the pUC8 vector. This plasmid comes from the plasmid pZ-1 (Norton and Coffin, 1985, Mol. Cell. Biol. 5:281), in which the vector pBR322 was replaced by pUC8. The lacZ gene was isolated from this plasmid through a double digestion with the enzymes KpnI and BamHI and this fragment was cloned in the plasmid p.PolyII.1 (Lathe et al., 1987, Gene 57:193) digested, in its turn, with the same enzymes KpnI and BamHI. This construction was given the name of pZIII.1.

Step 2: Cloning of the regulator region of the gene of the K6 keratin in the plasmid pZIII.1.

This cloning was carried out, in its turn, in various steps:

Step 2.1: Starting from the genome clone λ6 (Blessing et al., 1987, EMBO Journal. 6:567), which contains approximately 11 Kpb of the region preceding the gene of the bovine keratin and 4 Kpb of the coding region of the gene. The bovine genotheca from which this λ6 clone was isolated as well as the λA clone which will be mentioned below was constructed in the vector λEMBL3.

λ6 was directed with the enzymes EcoRI and BamHI which cut in the region which precedes the K6 gene in the −8.8 Kpb positions respectively. This fragment was inserted in the plasmid pBluescript (Stratagene) digested with the same enzymes, that is to say EcoRI and BamHI, to give rise to the plasmid pIVx5'E/B.

Step 2.2: Start from the genome cone λA (Blesing et al., 1987, op. cit.) which contains approximately 3.6 Kpb of the 5' region which precedes the bovine gene of K6 keratin, plus the entire coding region of the gene plus approximately 3Kpb of DNA in 3'. λA was digested with the enzymes BamHI and KpnI which cut in the positions −3.6 Kpb and +3 Kpb of the K6 gene respectively. This fragment was cloned in the plasmid pUC 18, digested with the same enzymes BamHI and KpnI, to give rise to the plasmid pIV*B/K.

Step 2.3: The insert pIV*5'E/B was separated from the vector by a double digestion with the enzymes SalI and BamHI. This fragment was cloned in the plasmid pIV*B/K, also digested with SalI and BamHI, to give rise to the plasmid pIV*S/K, which contained the 8.8 kpb which preceded the gene of the K6 bovine keratin plus 3Kpb of the coding region of the gene.

Step 2.4: The plasmid pIV*S/K was digested with SalI and NaeI (which cuts in the position +115 pb of the gene of the K6 keratin) to free a fragment which extends from the −8.8 Kpb position to the 115 pb position of the gene of the K6 keratin. This fragment was bound in the plasmid pZIII.1 previously digested with SalI and Asp718, the latter site being converted by treatment with the Klenow polymerase. The product of this ligation is the plasmid pKIV*Z(8.8) which contains the transgene which will be introduced within the genome of the transgenic animals.

Production of transgenic mice containing the recombinant construction pKIV*.Z(8.8)

The above-described plasmid pHIV*.Z(8.8) was directed with NotI (4 units of enzyme per µg off DNA for 1 hour at 370° C.), an enzyme located on both side of the multiple cloning site of the vector pPolyIII.1, in order to separate the insert, the transgene KIV*.Z(8.8) from the vector. The products of the digestion were subjected to an electrophoresis in a gel of 1% agarose of low melting point and the band of approximately 12 Kb containing the transgene was cut from the gel. In order to purify the transgene, the agarose was melted at 65° C., cooled to 37° C., and extracted with one volume of phenol. The aqueous phase of the extraction s was extracted with a volume of phenol/chloroform (1:1 v:v); the aqueous phase of this extraction was again extracted with one volume of chloroform and the DNA was precipitated from the aqueous phase of this last extraction with two volumes of ethanol at −70° C. and sedimented by centrifuging at 15,000 ×/g for 15 minutes. The DNA was dissolved in 500 µl of 0.2 M NaCl, 20 mM Tris-HCl (pH 7.5), 1 mM/EDTA, and purified additionally by filtration in a column of Elutip-d (Sleicher and Schuell) on 10 mM Tris-HCl (pH 7.5), 0.1 mM/EDTA. The DNA was precipitated with ethanol and dissolved to 2 µg/ml. Between 250 and 400 copies of the purified transgene were microinjected in the pronucleus of fertilized eggs in the one-cell stage in accordance with the methods described by Wagner et al., 1981 (op. cit.) and Hogan et al., 1986 (op. cit.). The eggs were obtained from hybrids C57B1/6J×balb/c; the mice were obtained from the Jackson Laboratories (U.S.A.).

After the microinjection, the eggs were incubated in M16 medium (Hogan et al., 1986, op. cit.) at 37° C. and 5% $CO_2$ overnight. On the following day, the eggs which had withstood the treatment were transferred to a pseudo-pregnant mother (previously paired with a vasectomized male) in accordance with well-established protocols (Gordon and Ruddle, 1983 [op. cit.]; Hogan et al., 1986 [op.cit.]). The imported embryos developed to term of the adoptive mother, the new mice being born at the end of 20 to 21 days.

All the animals were kept in a stable at 22° C., 50% humidity, with a cycle of 12 hours light/12 hours darkness.

At 3 weeks after delivery, the animals born were analyzed to determine which of them were transgenic, that is to say carriers of the transgene. For this, approximately 1 cm was sectioned under anesthesia from the tip of their tails. The DNA was extracted from this tissues basically in accordance with the method of Hogan et al, 1986 (op. cit.) by incubation overnight with proteinase K in the presence of 0.5% SDS, followed by two extractions with phenol:chloroform (1:1 v:v) and another extraction with chloroform. The nucleic acids were precipitated with ethanol at room temperature and redissolved in 250 µl of 10 mM Tris-HCl, pH 7.5, 1 mM/EDTA. Approximately 10 µg of DNA were digested with EcoRI, subjected to electrophoresis in gels of 1% agarose and transferred to nitrocellulose membranes, basically in accordance with the method described by Southern, 1975, J. Mol. Biol. 98:503. The nitrocellulose filters were hybridized at 42° C. with a radioactive probe for one night in a buffer solution containing 50% formamide, 5×SSC, 5×Denhardt solution, 1% SDS 10 mM Tris HCl, pH 7.5, 10% dextran sulfate. Thereupon they were washed twice in 2×SSC, 0.1% SDS at room temperature for 15 minutes and twice with 0.1×SSC, 0.1% SDS at 65° C. for 30 minutes, all in accordance with the method described by Maniatis et al., 1982 (op. cit.).

As radioactive probe there was used a HindIII/EcoRI fragment of the plasmid pRSV-lacZ-pUC8, containing the gene lacZ radioactively marked with a high specific activity by the method of Feinberg and Vogelstein, 1983, Anal. Biochem. 132:6. Hybridization indicated that four animals carried the transgene (between 5 and 50 copies) without any type of reorganization detectable by this technique. These four founder animals (1 male and 3 females) were crossed with hybrid mice C57b1/6J×balb/c of suitable sex and all transmitted the transgene to their descendants, it being possible to establish the corresponding transgenic lines.

Although described here for normal mice, the present invention is not limited to any given species of animal, but can be applied to any nonhuman species which provides a model of interest of human epidermis. For example, certain mutant mice characterized by a lack of hair, rabbits and hogs, to mention only a few, are animals in which transgenic skins of interest for man could be produced. Furthermore, as will be determined further below, the animals bearing the transgene KIV*.Z(8.8) can be good model systems for investigating substances and factors capable of stimulating the growth of hair. For these purposes, ewes would also be transgenic models of great interest.

Furthermore, other models different from the microinjection expressly described here can be used to produce transgenic animals, such as electroporation of DNA, transfection of DNA to embryonic cells, transfection of DNA to spermatozoa, etc.

Expression of the Transgene HIV*.Z(8.8) in Transgenic Mice

The activity of transgene in various tissues of transgenic mice was measured by visualizing in situ the amount of β-galactosidase produced by the cells of these tissues. For this, sections by freezing of 7–10 μm were incubated with X-gal in accordance with the method of Xothary et al., 1989, Development, 105:707, in such a manner that, depending on the amount of enzyme synthesized, the cells develop a blue color of greater or lesser intensity. For this, sections by freezing of 7–10 μm were washed with PBS and fixed for 5–20 minutes at 4° C. in 0.2% genteraldehyde in PBS. After being washed twice in PBS, they were incubated in the blue color developing mixture consisting of 0.04% a-chloro-5-bromo-3-indolylfl-β-D-galactopyranodium (X-gal, SIGMA), 1 mM $MgCl_2$, 10 mm potassium ferrocyanide and 10 mM protassium ferrocyanide. The incubation was continued for 2–18 hours, depending on the intensity of the color developed.

As can be seen from Table I, in which there are shown the tissue studied in which β-galactosidase activity existed or did not exist, the constituent expression pattern of the transgene was very similar to that of K6 keratin (compare Table I with Quinlan et al., 1985 [op. cit.]). Not only was expression detected in the suitable stratified epithelial tissues but, in addition, within it, there were the suprabasal cells which dyed blue, in accordance with what was expected if their expression was to emulate that of keratin K6.

The interfollicular skin of various regions of the body, including the tail, were in all the lines negative, in accordance with what was expected. In order to verify whether in this case the transgene is induced in those regions of the epidermis subjected to hyperproliferative stimuli, retinoic acid and TPA was applied topically to the tail of transgenic animals of the different lines. For this, employing the protocol of Schweizer et al. (op. cit.), the tail of the animals was topically treated for a period of 14 days, either daily with 30 μg of all-trans-retinoic acid (retinoic acid) dissolved in 100 μl of acetone or every two days with 20 nmol of TPA in 100 μl of acetone. As an alternative, the expression of the transgene was examined in wounds in process of cicatrization produced by us on the ears or produced spontaneously by the anima is themselves on their sides. There was also studied the expression of transgene in skin tumors of the back produced chemically by initiation with DMBA and promotion with TPA (Yuspa and Poitier, 1988, Adv. Cancer Res. 50:25). In all these cases, there was observed a strong induction of blue color in the suprabasal cells of the skin involved, which developed hyperplasia; this color was not observed in the untreated surrounding regions which, therefore, had remained histologically normal. On the tails of the animals treated with retinoic acid, it was verified by bi-dimensional gels (O'Farell et al., 1977, Cell 12:1133) that the induction of the blue color due to the transgene corresponded to the appearance of the endogenous K6 keratin. In order to determine at what moment of the treatment with retinoic acid the transgene was induced, the tails of seven mice of the same line were treated in the manner described above for 0, 3, 5, 7, 9, 11 and 14 days respectively. At the end of these times, the zone treated was removed from the tail under anesthesia. A portion of this tail was used for sectioning on a microtome and these sections were incubated in the presence of X-gal in order to observe whether a blue color developed. Tail skins of nontransgenic animals treated in the same manner were employed in order to extract RNA by the phenol/acid method as described by Chomezynski and Sacchi, 1992, Anal. Bioderm. 162:156). The total RNA thus extracted was analyzed by Northern type hybridizations in the following manner: 20 μg of RNA of each tail were subjected to electrophoresis in gels of 1% agarose, 1% formaldehyde and transferred to nitrocellulose filters in accordance with the method of Lerach et al., 1979, Biochemistry 16:4743. Thereupon, the filters were hybridized with a specific probe of the K6 keratin of mice (Finche et al., 1992, J. Invest. Dermatol.), radioactively marked, in a manner similar to that explained for the Southern type hybridizations described previously for the characterizing of the transgenic mice. It was observed that both the expression of the transgene visualized in the stainings with X-gal as well as that of the endogenous K6 keratin started after three days of treatment, both increasing progressively in parallel until reaching maxima on the ninth day of treatment. In other words, staining with X-gal of the skin sections of the transgenic mice of the invention developed a blue color which was detectable already at early moments of the treatment with retinoic acid and before a clear hyperplastic reaction appeared in the skin of the treated animals. This shows that the transgenic animals proposed in this invention as model system for the identification of agents which produce hyperproliferation of the skin, together with the method of detection proposed, constitute a very sensitive system which gives positive results with short times of treatment.

Another region of great interest in which expression of transgene was detected was in two parts of the hair follicle, namely the outer root sheath and the keratogenic zone of the bulb. In addition, in this latter zone, the blue color was only found in hair in early phase of growth, in anagen. This expression of the transgene in the keratogenous zone of the hair bulb as a function of the cycle was found in the hair of all the zones of the body investigated—tail, snout and trunk. Therefore, an additional property of this transgene would be its use in the detection of substances which stimulate the growth of the hair. The transgenic mice treated with these substances will have a greater density of hair with the keratogenous zone of the bulb capable of giving blue color. As an alternative, and based on similar reasoning, said transgenic animals can be used for the identification of substances which repress hair growth. The same type of reasoning can be applied to transgenic ewes with respect to the growth of wool, or any other animal of cattle of industrial interest.

Utility of the Transgenic Animals of the Invention

These animals can be used to identify agents which produce hyperproliferation in epidermis or protect against its appearance or cause it to regress once it has manifested itself. They may also be used in the identification of agents which alter, both positively and negatively, the growth cycle of the hair or the equivalents thereof in other species of animals, such as the wool of ewes.

The transgenic animals of the invention, together with the method proposed for detecting the transgene, constitute a sensitive, rapid model system. In addition to being based on the visualization of a molecular marker of easy detection, the method is, on the one hand, more objective and, on the other hand, simpler for the operator who carries it out than other methods commonly used to determine hyperproliferation, such as ones which count cell layers in the epidermis or judge the histological aspect of the cells of the basal layer and their cytoplasm/nucleus ratio, which methods require a high degree of experience and histological knowledge. Other methods of determining hyperproliferation used in the laboratory, such as the incorporation of radioactive thymidine by cells which divide actively are not very practical in a hospital or industrial context, due to their long length of time and the high degree of technical and practical specialization which they require on the part of the personnel which carries them out. Furthermore, in order to be able to be carry out the tests on the skin of the tail the animals suffer relatively little damage and it is not necessary to sacrifice them; furthermore, as only a small portion of the tail is required, a single animal can be used in more than one test. In the event that the tests are carried out on the skin of another part of the body, only a relatively small biopsy of the treated zone is required, the damage imparted to the animal being also only slight. And, since skin regenerates easily, one and the same animal can be used again for a long time.

Treatment and Detection

The agents to be investigated will be applied preferably topically on the skin of the animal, although they may also be ingested, injected or administered in any other more convenient manner.

In those experiments intended to determine the ability to produce hyperproliferation of a given substance, it will be applied topically either on the tail or on the back, preferably shaven. The induction of a blue color by incubation with X-gal of histological sections of the treated skin will be compared with similar sections of control animals treated only with the vehicle in which the substance being studied was dissolved. As an alternative, a positive control can be used, treating animals with retinoic acid or TPA following the protocols previously described, based on those used by Schweizer et al., 1987 (op. cit.).

If it is intended to check the possible hyperproliferation inhibiting or antiproliferative effect of a substance, the transgenic animals will be treated with this substance prior to or at the same time as another substance known for its ability to produce hyperproliferation, such as, for instance, TPA, retinoic acid, ultraviolet light, etc. The animals thus treated will be compared with other treated only with the hyperproliferation-producing agent. As an alternative, local hyperplasia will be induced in the transgenic animals by any known method or by any concrete object of study. Thereupon, a part of the animals will be treated with the substance the possible general concrete antiproliferative ability of which with respect to a given type of hyperplastic proliferation it is desired to determine. The rest of the animals will not be treated with this substance but will be left as controls with which the animals treated with the antiproliferative substance will be compared.

In order to study substances which may have an influence on hair growth, these substance will be applied preferably to the skin of the back. The density of hair showing, in histological sections incubated with X-gal, staining in the keratogenic zone of the bulb as compared with animals treated with the vehicle alone, will give a measure of the ability of the substance studied to stimulate or inhibit the growth.

In the case of both epidermal hyperproliferation and growth of the hair, there are model animals, in particular mutant mice (Lyon and Searle, 1989, *Genetic Variants and Strains of the Laboratory Mouse,* Oxford University Press—Gustav Fischer Verlag, publishers). In these cases, transgenic lines carrying the transgene KIV*.z(8.8) can be generated from these animals. Alternatively, the transgene could be transferred to mutant strains through suitable crosses with non-mutant strains carrying the transgene.

The method of detecting the activity of the agent under study will always be the visualizing of its action on the activity of the transgene. This visualizing will preferably be carried out by incubating histological sections of the skins of treated animals with X-gal, using the method previously described (see the section entitled "Expression of Transgene KIV*.Z(8.8 in transgenic mice"). Alternatively, if it is of interest to visualize the staining in larger zones, areas of several square millimeters can be surgically extracted and subjected to the same process of staining as the histological sections.

TABLE 1

SPECIFIC TISSUE EXPRESSION OF TRANSGENE pKIV*Z(8.8).

| | | |
|---|---|---|
| Epidermis: | Back | – |
| | Tail | – |
| | Plantar skin | +(suprabasal) |
| | Hair follicles and vibrissae | +(external root sheath and keratogenic zone) |
| Digestive Epithelia | Oral cavity | +(suprabasal) |
| | Tongue | +(suprabasal) |
| | Palate | +(suprabasal) |
| | Pharynx | +(suprabasal) |
| | Esophagus | +(suprabasal) |
| | Stomach | +(transition between glandular and aglandular zone) |
| Nasal Epithelium: | | + |
| Others: | Brain, liver, kidney, colon,) duodenum, pancreas, lung,) ) muscle, thymus, bladder, ) connective tissue. ) | Negative |

We claim:

1. A transgenic mouse whose germ cells and somatic cells contain a transgene comprising a nucleic acid sequence encoding a detectable marker selected from the group consisting of luciferase, chloramphenicol acetyl transferase, xanthine-guanine phosphoribosyl transferase, and beta-galactosidase operably linked to the 5' regulatory region of a bovine K6 gene, wherein said detectable marker is expressed in the keratogenous zone of the hair bulb and the epidermis and wherein said expression increases in response to administration of retinoic acid to said mouse.

2. A method of determining whether a treatment affects epidermal hyperproliferation or hair growth, said method comprising the steps of:
   a) subjecting the transgenic mouse of claim 1 to a treatment;
   b) measuring the expression of said detectable marker in the presence and absence of said treatment, wherein increased expression of said detectable marker in the presence of said treatment compared to the absence of said treatment indicates that said treatment increases hyperproliferation, and decreased expression of said detectable marker in the presence of said treatment compared to the absence of said treatment indicates that said treatment decreases hyperproliferation.

3. The method according to claim 2, wherein said treatment is administration of a compound.

4. The method according to claim 3, wherein said compound is administered topically.

5. The method according to claim 3, wherein said compound is administered orally.

6. The method according to claim 3, wherein said compound is administered intravenously, intramuscularly, or subcutaneously.

* * * * *